(12) United States Patent
Kim et al.

(10) Patent No.: US 7,049,482 B1
(45) Date of Patent: May 23, 2006

(54) NUCLEIC ACID MOLECULE ENCODING AN ARMADILLO REPEAT PROTEIN, ARIA AND A METHOD UTILIZING ARIA TO GENERATE SALT TOLERANT PLANTS

(75) Inventors: Soo Young Kim, Kwangju (KR); Hyung-in Choi, Kwangju (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 0 days.

(21) Appl. No.: 10/998,760

(22) Filed: Nov. 30, 2004

(51) Int. Cl.
*C12N 15/82* (2006.01)
(52) U.S. Cl. .................................................. 800/278
(58) Field of Classification Search ................ 800/288, 800/278; 536/23.1, 23.6; 435/320.1, 419, 435/468
See application file for complete search history.

(56) References Cited

FOREIGN PATENT DOCUMENTS

WO    WO 2004/035798 A2 *  4/2004

OTHER PUBLICATIONS

Kim et al. (2004) Plant Phys. vol. 136, pp. 3639-3648.*
Coates, Trends in Cell Biol, vol. 13, No. 9, Sep. 2003, Armadillo repeat proteins: beyond the animal kingdom.
Ryals et al, The Plant Cell, vol. 9, Mar. 1997, pp. 425-439, The Arabidopsis NIM1 Protein Shows Homology to the Mammalian . . .
Gu et al, Proc Natl Acad Sci, vol. 95, Jan. 1998, pp. 382-387, Binding of an arm repeat protein to the kinase domain of the . . .
Cao et al, CELL, vol. 88, Jan. 10, 1997, pp. 57-63, The Arabidopsis NPR1 Gene That Controls Systemic Acquired . . .
Choi et al, Jour of Biol Chem, vol. 275, No. 3, Jan. 21, 2000, pp. 1723-1730, ABFs, a Family of ABA-responsive Element Binding . . .
Amador et al, CELL, vol. 106, Aug. 10, 2001, pp. 343-354, Gibberellins Signal Nuclear Import of PHOR1, A Photoperiod . . .
Kim et al, The Plant Jour, vol. 40, 2004, pp. 75-87, ABF2, an ABRE-binding bZIP factor, is an essential component of glucose . . .

* cited by examiner

*Primary Examiner*—Ashwin D. Mehta
*Assistant Examiner*—Cathy Kingdon Worley
(74) *Attorney, Agent, or Firm*—Jacobson Holman PLLC

(57) ABSTRACT

The present invention relates to a gene encoding a protein named as ARIA (armadillo repeat protein interacting with ABF2), which contains armadillo repeats and a BTB/POZ domain. The protein is a novel ABA signaling component, which affects ABA-regulated gene expression, seedling growth, ABA sensitivity, and stress tolerance of plants. Furthermore, the present invention provides a method of producing salt-tolerant plants comprising the introduction of an expression cassette containing the ARIA gene linked to a plant promoter to plants.

1 Claim, 5 Drawing Sheets

SEQUENCE LISTING

<160> NUMBER OF SEQ ID NOS: 13

<210> SEQ ID NO 1
<211> LENGTH: 2130
<212> TYPE: DNA
<213> ORGANISM: Arabidopsis sp.

<400> SEQUENCE: 1

| | | | | | |
|---|---|---|---|---|---|
| atggaccaac | aaccggagag | gcgagaaggc | cggagttttc | cggagcgtaa | aggacagaag | 60 |
| cggaagctag | aggaaggagc | cgccgccgta | gaagatcgag | agatctctgc | cgtcagcacc | 120 |
| gacggaggcc | aagcgcttct | tagcgaggtt | gctgctcaag | tctcggtact | aaactctgcc | 180 |
| ttctcttggc | aagagtccga | tcgcgctgct | gccaagcgac | ccactcaagt | tctggctgag | 240 |
| ctagccaaaa | acgaggattt | agtgaacgtg | attgtcgacg | gaggtgctgt | tccagctctt | 300 |
| atgacgcatc | tacaggcgcc | accatacaac | gacgggact | tggctgagaa | gccgtacgaa | 360 |
| cacgaagttg | agaagggaag | cgcttttgcg | cttggtcttc | ttgctattaa | gccagagtat | 420 |
| cagaaactga | tagtagacaa | aggtgcctta | cctcatttag | tgaatttgtt | gaagagaaac | 480 |
| aaagatggtt | ctagctctcg | agctgtgaat | agtgttatca | gaagagcggc | tgatgccatc | 540 |
| accaatcttg | ctcatgagaa | cagcagtatc | aagacccgtg | ttagggtaga | aggcggtatt | 600 |
| ccacctctcg | tggagttgct | tgaatttct | gattcaaagg | tccagagagc | agcagcaggg | 660 |
| gcattgagaa | cccttgcatt | taaaaatgat | gataacaaga | atcagatagt | tgaatgcaat | 720 |
| gctcttccca | cacttattct | aatgctagga | tcagaggatg | ctgctataca | ttatgaagcg | 780 |
| gttggagtta | taggcaatct | agtacactcg | tctccacaca | ttaaaaaga | ggttcttact | 840 |
| gccgggggcgt | tgcaacctgt | cattggtctt | cttagctcct | gttgccctga | gagtcaaaga | 900 |
| gaggcggctt | tattacttgg | gcagtttgcc | tcaactgatt | ctgattgtaa | ggtgcacatt | 960 |
| gtgcaaaggg | gtgctgtccg | tcctttaatt | gagatgcttc | agtccccgga | tgtccagttg | 1020 |
| aaggaaatgt | cggccttgc | actgggtaga | ttggcacagg | atgccacaa | tcaagctggt | 1080 |
| attgcccata | gtggtggttt | aggaccttta | ttgaagcttc | tcgattcaag | aaatggatca | 1140 |
| ttgcaacaca | atgctgcatt | tgctctttat | ggccttgccg | ataatgagga | taatgtgtca | 1200 |
| gattttatca | gggtgggagg | tatccaaaag | ctacaggatg | gagagtttat | tgttcaagca | 1260 |
| actaaagatt | gtgttttccaa | aacactaaag | agattggagg | agaagattca | tggaagagtt | 1320 |
| ctgagacatc | tgttgtacct | aatgcgcatt | tcagagaagt | ctatccaaag | acgagttgct | 1380 |
| cttgcccttg | ctcatctctg | ttcacccgag | gatcaacgaa | ccatattcat | agatgacaac | 1440 |
| gggttggagt | tgctactcgg | tcttcttggt | tcttaaaca | ctaagcagca | acttgacggt | 1500 |
| gcagcagcgt | tgtacaaatt | agcaaataaa | tctatggcac | tttctccagt | tgatgctgct | 1560 |
| cctccttctc | caacacaaag | ggtttatctc | ggagagcaat | atgtaaataa | tgctacgctg | 1620 |
| tctgatgtaa | cctttctagt | cgaaggaagg | acattctatg | cacacagaat | ttgtctgctg | 1680 |
| gcatcctcag | atgcatttcg | tgcaatgttt | gatggtggtt | acagagaaaa | agacgctaga | 1740 |
| gatattgaga | ttccaaatat | caaatgggag | gtgtttgagt | taatgatgag | gtttatatac | 1800 |
| actgatctg | tcgacataac | aaatgagata | tcaaagatc | ttctaagagc | agcggatcag | 1860 |
| tatctcttgg | agggcctgaa | acgactctgt | gaatacacaa | ttgctcagga | tattacgttg | 1920 |
| gaaagtatag | agacatgta | cgagctatca | gaagcattcc | atgcgatgtc | gctgaggcaa | 1980 |
| gcttgtatca | tgttcatcct | ggagcatttc | gataaactga | gttcaatgcc | ttggcagaac | 2040 |

```
gagctggtgc agagaacaat accagagata agagagtact tttgtagagc cctaacaaag    2100
tctactacaa acctgcaaag cttgaggttg                                     2130
```

<210> SEQ ID NO 2
<211> LENGTH: 710
<212> TYPE: PRT
<213> ORGANISM: Arabidopsis sp.

<400> SEQUENCE: 2

```
Met Asp Gln Gln Pro Glu Arg Arg Glu Gly Arg Ser Phe Pro Glu Arg
1               5                   10                  15

Lys Gly Gln Lys Arg Lys Leu Glu Glu Gly Ala Ala Ala Val Glu Asp
            20                  25                  30

Arg Glu Ile Ser Ala Val Ser Thr Asp Gly Gly Gln Ala Leu Leu Ser
        35                  40                  45

Glu Val Ala Ala Gln Val Ser Val Leu Asn Ser Ala Phe Ser Trp Gln
50                  55                  60

Glu Ser Asp Arg Ala Ala Ala Lys Arg Ala Thr Gln Val Leu Ala Glu
65                  70                  75                  80

Leu Ala Lys Asn Glu Asp Leu Val Asn Val Ile Val Asp Gly Gly Ala
                85                  90                  95

Val Pro Ala Leu Met Thr His Leu Gln Ala Pro Tyr Asn Asp Gly
            100                 105                 110

Asp Leu Ala Glu Lys Pro Tyr Glu His Glu Val Glu Lys Gly Ser Ala
        115                 120                 125

Phe Ala Leu Gly Leu Leu Ala Ile Lys Pro Glu Tyr Gln Lys Leu Ile
130                 135                 140

Val Asp Lys Gly Ala Leu Pro His Leu Val Asn Leu Leu Lys Arg Asn
145                 150                 155                 160

Lys Asp Gly Ser Ser Ser Arg Ala Val Asn Ser Val Ile Arg Arg Ala
                165                 170                 175

Ala Asp Ala Ile Thr Asn Leu Ala His Glu Asn Ser Ser Ile Lys Thr
            180                 185                 190

Arg Val Arg Val Glu Gly Gly Ile Pro Pro Leu Val Glu Leu Leu Glu
        195                 200                 205

Phe Ser Asp Ser Lys Val Gln Arg Ala Ala Ala Gly Ala Leu Arg Thr
210                 215                 220

Leu Ala Phe Lys Asn Asp Asp Asn Lys Asn Gln Ile Val Glu Cys Asn
225                 230                 235                 240

Ala Leu Pro Thr Leu Ile Leu Met Leu Gly Ser Glu Asp Ala Ala Ile
                245                 250                 255

His Tyr Glu Ala Val Gly Val Ile Gly Asn Leu Val His Ser Ser Pro
            260                 265                 270

His Ile Lys Lys Glu Val Leu Thr Ala Gly Ala Leu Gln Pro Val Ile
        275                 280                 285

Gly Leu Leu Ser Ser Cys Cys Pro Glu Ser Gln Arg Glu Ala Ala Leu
290                 295                 300

Leu Leu Gly Gln Phe Ala Ser Thr Asp Ser Asp Cys Lys Val His Ile
305                 310                 315                 320

Val Gln Arg Gly Ala Val Arg Pro Leu Ile Glu Met Leu Gln Ser Pro
                325                 330                 335

Asp Val Gln Leu Lys Glu Met Ser Ala Phe Ala Leu Gly Arg Leu Ala
            340                 345                 350
```

-continued

```
Gln Asp Ala His Asn Gln Ala Gly Ile Ala His Ser Gly Gly Leu Gly
            355                 360                 365

Pro Leu Leu Lys Leu Leu Asp Ser Arg Asn Gly Ser Leu Gln His Asn
    370                 375                 380

Ala Ala Phe Ala Leu Tyr Gly Leu Ala Asp Asn Glu Asp Asn Val Ser
385                 390                 395                 400

Asp Phe Ile Arg Val Gly Gly Ile Gln Lys Leu Gln Asp Gly Glu Phe
                405                 410                 415

Ile Val Gln Ala Thr Lys Asp Cys Val Ser Lys Thr Leu Lys Arg Leu
            420                 425                 430

Glu Lys Ile His Gly Arg Val Leu Arg His Leu Leu Tyr Leu Met
            435                 440                 445

Arg Ile Ser Glu Lys Ser Ile Gln Arg Val Ala Leu Ala Leu Ala
    450                 455                 460

His Leu Cys Ser Pro Glu Asp Gln Arg Thr Ile Phe Ile Asp Asn
465                 470                 475                 480

Gly Leu Glu Leu Leu Leu Gly Leu Leu Gly Ser Leu Asn Thr Lys Gln
                485                 490                 495

Gln Leu Asp Gly Ala Ala Leu Tyr Lys Leu Ala Asn Lys Ser Met
            500                 505                 510

Ala Leu Ser Pro Val Asp Ala Ala Pro Pro Ser Pro Thr Gln Arg Val
            515                 520                 525

Tyr Leu Gly Glu Gln Tyr Val Asn Asn Ala Thr Leu Ser Asp Val Thr
    530                 535                 540

Phe Leu Val Glu Gly Arg Thr Phe Tyr Ala His Arg Ile Cys Leu Leu
545                 550                 555                 560

Ala Ser Ser Asp Ala Phe Arg Ala Met Phe Asp Gly Gly Tyr Arg Glu
                565                 570                 575

Lys Asp Ala Arg Asp Ile Glu Ile Pro Asn Ile Lys Trp Glu Val Phe
            580                 585                 590

Glu Leu Met Met Arg Phe Ile Tyr Thr Gly Ser Val Asp Ile Thr Asn
    595                 600                 605

Glu Ile Ser Lys Asp Leu Leu Arg Ala Ala Asp Gln Tyr Leu Leu Glu
610                 615                 620

Gly Leu Lys Arg Leu Cys Glu Tyr Thr Ile Ala Gln Asp Ile Thr Leu
625                 630                 635                 640

Glu Ser Ile Gly Asp Met Tyr Glu Leu Ser Glu Ala Phe His Ala Met
                645                 650                 655

Ser Leu Arg Gln Ala Cys Ile Met Phe Ile Leu Glu His Phe Asp Lys
            660                 665                 670

Leu Ser Ser Met Pro Trp Gln Asn Glu Leu Val Gln Arg Thr Ile Pro
    675                 680                 685

Glu Ile Arg Glu Tyr Phe Cys Arg Ala Leu Thr Lys Ser Thr Thr Asn
690                 695                 700

Leu Gln Ser Leu Arg Leu
705                 710
```

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3

-continued gctagtggtg tggttccagt t 21

<210> SEQ ID NO 4
<211> LENGTH: 32
<212> TYPE: DNA
<213> ORGANISM: Artificial
<220> FEATURE:
<223> OTHER INFORMATION: Primer

<400> SEQUENCE: 4
gagagctcga gctgagctct tgcagcaacc tg 32

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ccaatcatgc ctaagcagcc 20

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
gagagctcga gctctacaac tttctccaca gtg 33

<210> SEQ ID NO 7
<211> LENGTH: 24
<212> TYPE: DNA
<213> ORGANISM: Artificial
<220> FEATURE:
<223> OTHER INFORMATION: Primer

<400> SEQUENCE: 7
ggatcgtctt ttactttgtg aacg 24

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
cattcaagac cgattgtgat cag 23

<210> SEQ ID NO 9
<211> LENGTH: 22
<212> TYPE: DNA
<213> ORGANISM: Artificial
<220> FEATURE:
<223> OTHER INFORMATION: Primer

<400> SEQUENCE: 9
gatccgaaga agaggagaga tc 22

<210> SEQ ID NO 10
<211> LENGTH: 38
<212> TYPE: DNA
<213> ORGANISM: Artificial

-continued

```
<220> FEATURE:
<223> OTHER INFORMATION: Primer

<400> SEQUENCE: 10
gccacgctgt cttctttcac tacactaaaa aatacagc                                    38

<210> SEQ ID NO 11
<211> LENGTH: 30
<212> TYPE: DNA
<213> ORGANISM: Artificial
<220> FEATURE:
<223> OTHER INFORMATION: Primer

<400> SEQUENCE: 11
cgcggatcca tggaccaaca accggagagg                                             30

<210> SEQ ID NO 12
<211> LENGTH: 32
<212> TYPE: DNA
<213> ORGANISM: Artificial
<220> FEATURE:
<223> OTHER INFORMATION: Primer

<400> SEQUENCE: 12
gcgggatccc aacctcaagc tttgcaggtt tg                                          32

<210> SEQ ID NO 13
<211> LENGTH: 710
<212> TYPE: PRT
<213> ORGANISM: Arabidopsis sp.

<400> SEQUENCE: 13
```

Met Asp Gln Gln Pro Glu Arg Arg Glu Gly Arg Ser Phe Pro Glu Arg
1               5                   10                  15

Lys Gly Gln Lys Arg Lys Leu Glu Glu Gly Ala Ala Ala Val Glu Asp
            20                  25                  30

Arg Glu Ile Ser Ala Val Ser Thr Asp Gly Gly Gln Ala Leu Leu Ser
        35                  40                  45

Glu Val Ala Ala Gln Val Ser Val Leu Asn Ser Ala Phe Ser Trp Gln
    50                  55                  60

Glu Ser Asp Arg Ala Ala Ala Lys Arg Ala Thr Gln Val Leu Ala Glu
65                  70                  75                  80

Leu Ala Lys Asn Glu Asp Leu Val Asn Val Ile Val Asp Gly Gly Ala
                85                  90                  95

Val Pro Ala Leu Met Thr His Leu Gln Ala Pro Tyr Asn Asp Gly
            100                 105                 110

Asp Leu Ala Glu Lys Pro Tyr Glu His Glu Val Glu Lys Gly Ser Ala
        115                 120                 125

Phe Ala Leu Gly Leu Leu Ala Ile Lys Pro Glu Tyr Gln Lys Leu Ile
    130                 135                 140

Val Asp Lys Gly Ala Leu Pro His Leu Val Asn Leu Leu Lys Arg Asn
145                 150                 155                 160

Lys Asp Gly Ser Ser Arg Ala Val Asn Ser Val Ile Arg Arg Ala
                165                 170                 175

Ala Asp Ala Ile Thr Asn Leu Ala His Glu Asn Ser Ser Ile Lys Thr
        180                 185                 190

Arg Val Arg Val Glu Gly Gly Ile Pro Pro Leu Val Glu Leu Leu Glu
    195                 200                 205

Phe Ser Asp Ser Lys Val Gln Arg Ala Ala Ala Gly Ala Leu Arg Thr

```
              210                 215                 220
Leu Ala Phe Lys Asn Asp Asp Asn Lys Asn Gln Ile Val Glu Cys Asn
225                 230                 235                 240

Ala Leu Pro Thr Leu Ile Leu Met Leu Gly Ser Glu Asp Ala Ala Ile
                245                 250                 255

His Tyr Glu Ala Val Gly Val Ile Gly Asn Leu Val His Ser Ser Pro
                260                 265                 270

His Ile Lys Lys Glu Val Leu Thr Ala Gly Ala Leu Gln Pro Val Ile
                275                 280                 285

Gly Leu Leu Ser Ser Cys Cys Pro Ser Gln Arg Glu Ala Ala Leu
290                 295                 300

Leu Leu Gly Gln Phe Ala Ser Thr Asp Ser Asp Cys Lys Val His Ile
305                 310                 315                 320

Val Gln Arg Gly Ala Val Arg Pro Leu Ile Glu Met Leu Gln Ser Pro
                325                 330                 335

Asp Val Gln Leu Lys Glu Met Ser Ala Phe Ala Leu Gly Arg Leu Ala
                340                 345                 350

Gln Asp Ala His Asn Gln Ala Gly Ile Ala His Ser Gly Gly Leu Gly
                355                 360                 365

Pro Leu Leu Lys Leu Leu Asp Ser Arg Asn Gly Ser Leu Gln His Asn
370                 375                 380

Ala Ala Phe Ala Leu Tyr Gly Leu Ala Asp Asn Glu Asp Asn Val Ser
385                 390                 395                 400

Asp Phe Ile Arg Val Gly Gly Ile Gln Lys Leu Gln Asp Gly Glu Phe
                405                 410                 415

Ile Val Gln Ala Thr Lys Asp Cys Val Ser Lys Thr Leu Lys Arg Leu
                420                 425                 430

Glu Glu Lys Ile His Gly Arg Val Leu Arg His Leu Leu Tyr Leu Met
                435                 440                 445

Arg Ile Ser Glu Lys Ser Ile Gln Arg Arg Val Ala Leu Ala Leu Ala
450                 455                 460

His Leu Cys Ser Pro Glu Asp Gln Arg Thr Ile Phe Ile Asp Asp Asn
465                 470                 475                 480

Gly Leu Glu Leu Leu Leu Gly Leu Leu Gly Ser Leu Asn Thr Lys Gln
                485                 490                 495

Gln Leu Asp Gly Ala Ala Leu Tyr Lys Leu Ala Asn Lys Ser Met
                500                 505                 510

Ala Leu Ser Pro Val Asp Ala Ala Pro Pro Ser Pro Thr Gln Arg Val
                515                 520                 525

Tyr Leu Gly Glu Gln Tyr Val Asn Asn Ala Thr Leu Ser Asp Val Thr
                530                 535                 540

Phe Leu Val Glu Gly Arg Thr Phe Tyr Ala His Arg Ile Cys Leu Leu
545                 550                 555                 560

Ala Phe Ser Asp Ala Phe Arg Ala Met Phe Asp Gly Tyr Arg Glu
                565                 570                 575

Lys Asp Ala Arg Asp Ile Glu Ile Pro Asn Ile Lys Trp Glu Val Phe
                580                 585                 590

Glu Leu Met Met Arg Phe Ile Tyr Thr Gly Ser Val Asp Ile Thr Asn
                595                 600                 605

Glu Ile Ser Lys Asp Leu Leu Arg Ala Ala Asp Gln Tyr Leu Leu Glu
                610                 615                 620

Gly Leu Lys Arg Leu Cys Glu Tyr Thr Ile Ala Gln Asp Ile Thr Leu
625                 630                 635                 640
```

-continued

```
Glu Ser Ile Gly Asp Met Tyr Glu Leu Ser Glu Ala Phe His Ala Met
            645                 650                 655

Ser Leu Arg Gln Ala Cys Ile Met Phe Ile Leu Glu His Phe Asp Lys
            660                 665                 670

Leu Ser Ser Met Pro Trp Gln Asn Glu Leu Val Gln Arg Thr Ile Pro
            675                 680                 685

Glu Ile Arg Glu Tyr Phe Cys Arg Ala Leu Thr Lys Ser Thr Thr Asn
        690                 695                 700

Leu Gln Ser Leu Arg Leu
705                 710
```

NUCLEIC ACID MOLECULE ENCODING AN ARMADILLO REPEAT PROTEIN, ARIA AND A METHOD UTILIZING ARIA TO GENERATE SALT TOLERANT PLANTS

FIELD OF THE INVENTION

This invention relates to a nucleic acid molecule encoding an armadillo repeat protein (referred to "ARIA") and the method for increasing salt tolerance of plants using an expression cassette comprising the ARIA gene operably linked to a plant promoter.

BACKGROUND OF THE INVENTION

Armadillo (arm) repeat is a 42 amino acid protein—protein interaction motif (Peifer et al., 1994; Hatzfeld, 1999; Andrade et al., 2001). The repeat was first identified in the Drosophila segment polarity gene armadillo (Riggleman, 1989) and since then in many eukaryotic proteins involved in cell signaling or cellular architecture. Armadillo and its vertebrate homolog β-catenin are components of the Wingless and the Wnt signaling pathways, which determine the patterning of Drosophila embryo body segments and vertebrate cell fates, respectively (Polakis, 2000). When triggered by the Wingless or Wnt growth factor signal, otherwise unstable armadillo/β-catenin becomes stabilized, translocates into the nucleus, and, together with the TCF/LEF subfamily of transcription factors, activates the Wingless/Wnt target genes. β-catenin also plays a structural role in cell—cell adhesion, by linking the transmembrane adhesion molecules cadherins to actin cytoskeleton.

Pfam (http://www.sanger.ac.uk/Software/Pfam/) and SMART (http://smart.embl-heidelberg.de/) protein databases enlist more than 90 Arabidopsis arm repeat proteins. Based on their sequence homology, these proteins can be grouped into several different subfamilies such as impotin-α, kinesin, and U-box protein families (Coates, 2003). However, the functions of the Arabidopsis and other plant arm repeat proteins have not been characterized in detail except those of ARC1 and PHOR1. ARC1 interacts with an S-locus receptor kinase of Brassica (Gu et al., 1998) and has been demonstrated to be a positive regulator of the self-incompatibility response (Stone et al., 1999). A recent study shows that ARC1 promotes ubiquitination and proteasomal degradation of compatibility factors in pistil (Stone et al., 2003). The potato arm repeat protein PHOR1, on the other hand, is involved in gibberellin (GA) signaling (Amador et al., 2001). Antisense suppression of its expression reduces GA sensitivity and plant height, whereas its overexpression increases GA sensitivity and internode length.

BTB (BR-C, ttk, and bab) domain is another evolutionarily conserved protein—protein interaction domain (Bardwell and Treisman, 1994; Zollman et al., 1994). The ~120 amino acid motif, also known as POZ (poxvirus and zinc finger) domain, was first identified in a group of poxvirus proteins and in Drosophila zinc finger proteins, Broad-Complex (BR-C), Tramtrak (Ttk), and Bric-a-brac (bab). Subsequently, it has been found that the BTB/POZ domain is present in 5–10% of zinc finger transcription factors and in some actin-binding proteins or ion channels (Aravind and Koonin, 1998; Collins et al., 2001). Arabidopsis genome contains approximately 80 BTB domain proteins. However, only three of them have been reported to date: NPH3 and RPT2, signal transducers of phototrophic response (Motchoulski and Liscum, 1999; Sakai et al., 2000), and NPR1/NIM1, a regulator of gene expression during systemic acquired response (Cao et al., 1997; Ryals et al., 1997).

Plant hormone abscisic acid (ABA) controls various aspects of plant growth and development (Finkelstein et al., 2002). It inhibits germination and postgermination growth at high concentrations, although it is necessary for normal seedling growth. It regulates seed maturation process and prevents embryos from precocious germination. During vegetative growth, ABA plays an essential role in adaptation to various abiotic stresses such as drought, high salinity and cold (Xiong et al., 2002). Extensive genetic and biochemical studies have been done to identify the regulatory components of various aspects of ABA response. As a consequence, a large number of ABA signaling components have been reported that include transcription factors, kinases/phosphatases, RNA-binding proteins, G-proteins, and secondary messengers (Finkelstein et al., 2002; Xiong et al., 2002).

During vegetative growth, ABA controls the expression of numerous genes associated with adaptive responses to drought and other abiotic stresses (Ramanulu and Bartels, 2002; Shinozaki et al., 2003). The ABA-regulation of stress-responsive genes is largely mediated by cis-regulatory elements sharing the CACGTGGC consensus. Previously, we and others identified a small subfamily of basic leucine zipper (bZIP) class transcription factors that interact with the elements (Choi et al., 2000; Uno et al., 2000). We subsequently showed that the factors, named as ABFs (i.e., ABF1–ABF4) or AREBs (i.e., AREB1–AREB3), are involved in ABA and various abiotic stress responses (Kang et al., 2002; Kim et al., 2004). In particular, ABF2/AREB1, which will be referred to as ABF2 hereafter, regulates seedling growth rate and plays an essential role in glucose-induced developmental arrest process. Its overexpression phenotypes such as altered ABA sensitivity and multiple stress tolerance also suggest that it is involved in ABA and stress responses. We are interested in delineating the ABA signaling pathway(s) that lead to the ABF-dependent ABA/stress-responsive gene expression in vegetative tissues. Toward this end, we carried out two-hybrid screens to isolate proteins that interact with ABF family members to modulate their activities. Here, we describe an arm repeat and BTB/POZ domain protein that interacts with ABF2. In vivo analysis of its function revealed that the ABF2-interacting protein is a novel ABA signaling component that regulates seed germination, seedling growth, glucose response, and ABA/stress responses. In particular, overexpression of ARIA in Arabidopsis results in enhanced seedling survival under high salt conditions, indicating that it can be utilized to develop salt-tolerant plants.

SUMMARY OF THE INVENTION

The present invention relates to a gene encoding a protein named as ARIA (armadillo repeat protein interacting with ABF2), which contains armadillo repeats and a BTB/POZ domain. The protein is a novel ABA signaling component, which affects ABA-regulated gene expression, seedling growth, ABA sensitivity, and stress tolerance of plants. Furthermore, the present invention provides a method of producing salt-tolerant plants comprising the introduction of an expression cassette containing the ARIA gene linked to a plant promoter to plants.

BRIEF DESCRIPTION OF THE DRAWINGS

FIG. 1 Summary of the two-hybrid screens to isolate ABF2-interacting proteins. A, Schematic diagram of ABF2 and the fragments used in the two-hybrid screens. The regions conserved among ABF family members are shown as boxes. S and T denote serine and threonine residues, respectively, that are putative phosphorylation sites. The glutamine-rich (Q) and the bZIP (bZIP) regions are also indicated. The thick bars indicate the fragments used for the bait constructs, with the amino acid position numbers in parentheses. The full-length ABF2 is consisted of 416 amino acid residues. B, Specificity of interaction. The interaction between a Group2 positive clone (clone 20) and ABF2 (amino acids 234–337), nuclear lamin, ABF3 (amino acids 274–373), or ABF4 (amino acids 265–352) was tested. Yeast containing each bait construct was transformed with the positive clone, transformants were patched on a SC-Leu medium, and growth was examined after 4 days to test the LEU2 reporter activity. C, Deduced amino acid sequence of ARIA (SEQ ID NO: 13). The arm repeat region is shaded, and the BTB/POZ domain is underlined. The predicted nuclear localization signal in the N-terminal region is indicated in bold. Below, the conserved motifs are also shown schematically. arm repeats 1, 8, and 9 are less-well conserved. D, In vitro interaction of ABF2 and ARIA. Left, Coomassie Blue-stained gel of GST alone (GST) and GST-ARIA fusion proteins containing the full-length ARIA (Full), the arm repeat region (ARM) (amino acids 1–518), or the BTB domain (BTB) (amino acids 511–710), respectively. Right, GST pulldown assay. An autoradiogram showing in vitro-translated, $^{35}$S-Met-labelled ABF2 retained by the GST-ARIA fusion proteins. The same amounts of recombinant proteins were used in the assay. The arrows indicate the position of protein bands. The Y-axis shows the molecule weight markers for protein (31, 45, 66.2, 97.4).

Figure 2:
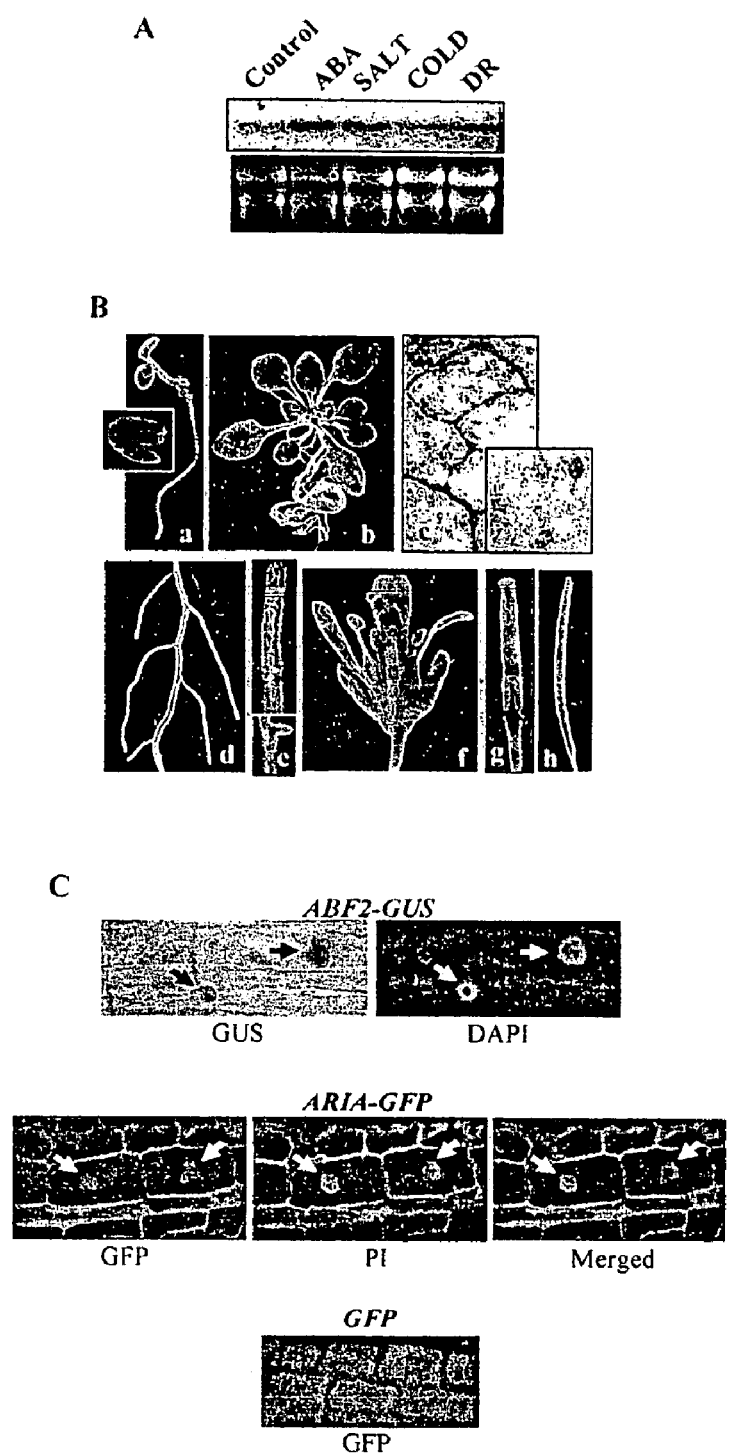

FIG. 2 Expression patterns of ARIA. A, RNA gel blot analysis. RNA was isolated from seedlings treated with 100 μM ABA, 250 mM NaCl, cold (24 hr at 4° C.) or dehydration (withholding from water for two weeks). Bottom panel shows the ethidium bromide-stained gel. B, Histochemical GUS staining of transgenic plants transformed with a 2.1 kb ARIA promoter-GUS reporter construct. T2 or T3 generation plants were stained with X-gluc (5-bromo-4-chloro-3-indolyl-β-glucuronic acid) for 24 hr. a, three-day-old seedling. The inset shows a mature embryo from a dry silique. b, two-week-old seedling. c, leaf. d, e, root. f, flower. g, immature silique. h, mature silique. C, Subcellular localization of ABF2 and ARIA. The top panel shows the light microscopy images of onion cells transiently transformed with a 35S-ABF2-GUS fusion construct and stained with X-gluc (GUS) or 4',6-diamino-2-phenylindole (DAPI). Middle and bottom panels show the confocal images of root cells of a plant transformed with 35S-ARIA-GFP (ARIA-GFP) or $^{35}$S-GFP (GFP). GFP, GFP channel. PI, cells stained with propidium iodide. The arrows denote nuclei.

Figure 3:
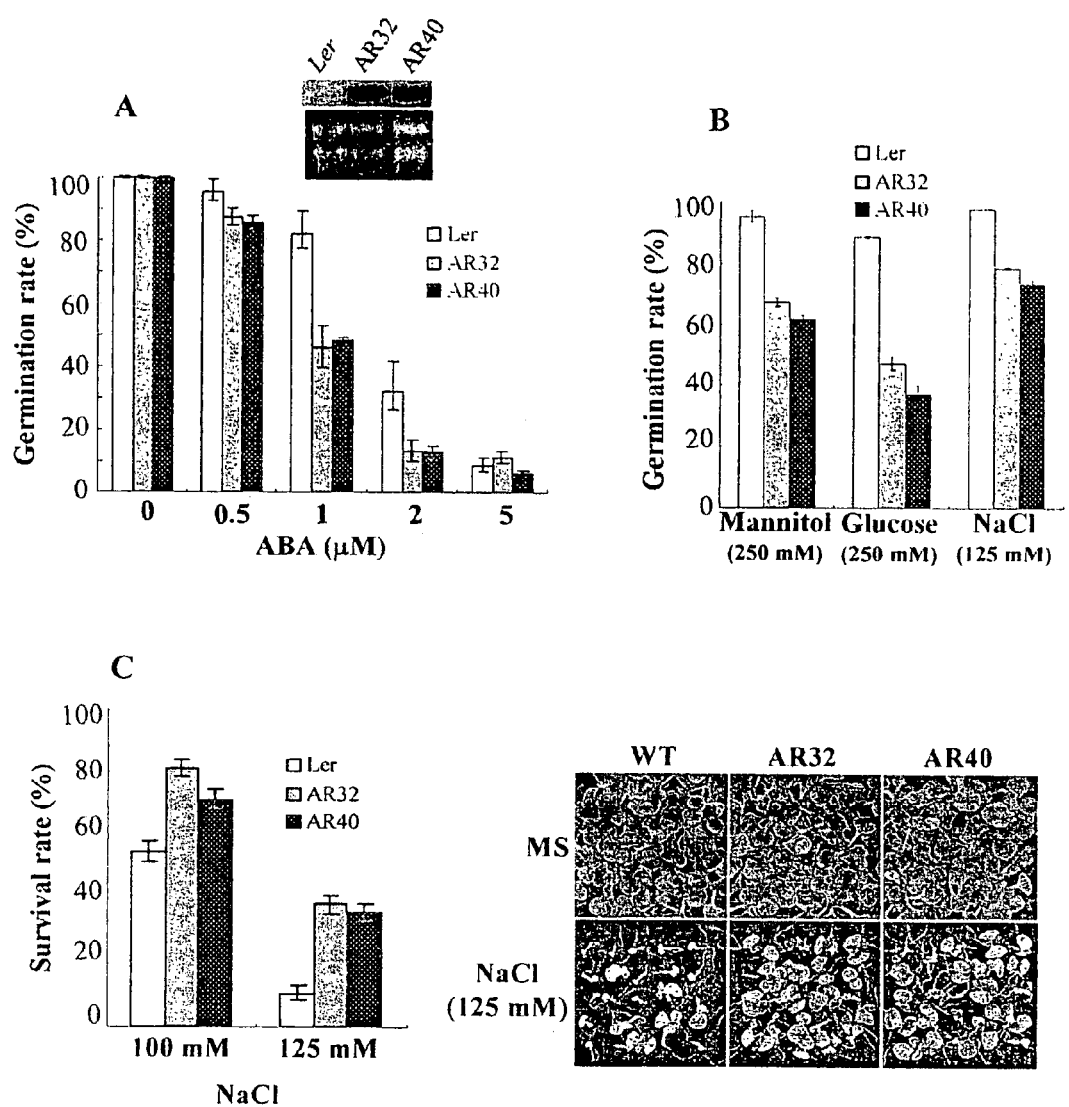

FIG. 3 Phenotypes of 35S-ARIA plants. A, ABA dose-response of germination. Seeds were cold-treated for 5 days at 4° C. and plated on sucrose-free MS medium containing various concentrations of ABA. Germination (full-emergence of radicle) was scored after 3 days. Experiments were done in triplicates (n=36 each), and the small bars indicate standard errors. B, Osmolarity sensitivity of germination. Germination assay was performed as in (A) on MS media containing various concentrations of mannitol, glucose or NaCl, and the germination rates at 250 mM mannitol, 250 mM glucose and 125 mM NaCl are presented. Experiments were done in triplicates (n=36 each). C, Salt tolerance. Left, survival rates of seedlings under high salt conditions. Seeds were germinated and grown on MS media containing 100 mM or 125 mM NaCl for 2 weeks, and survival rates were determined. The Experiments were done in triplicates (n=50 each). Right, representative seedlings grown at 125 mM NaCl for 15 days.

Figure 4:
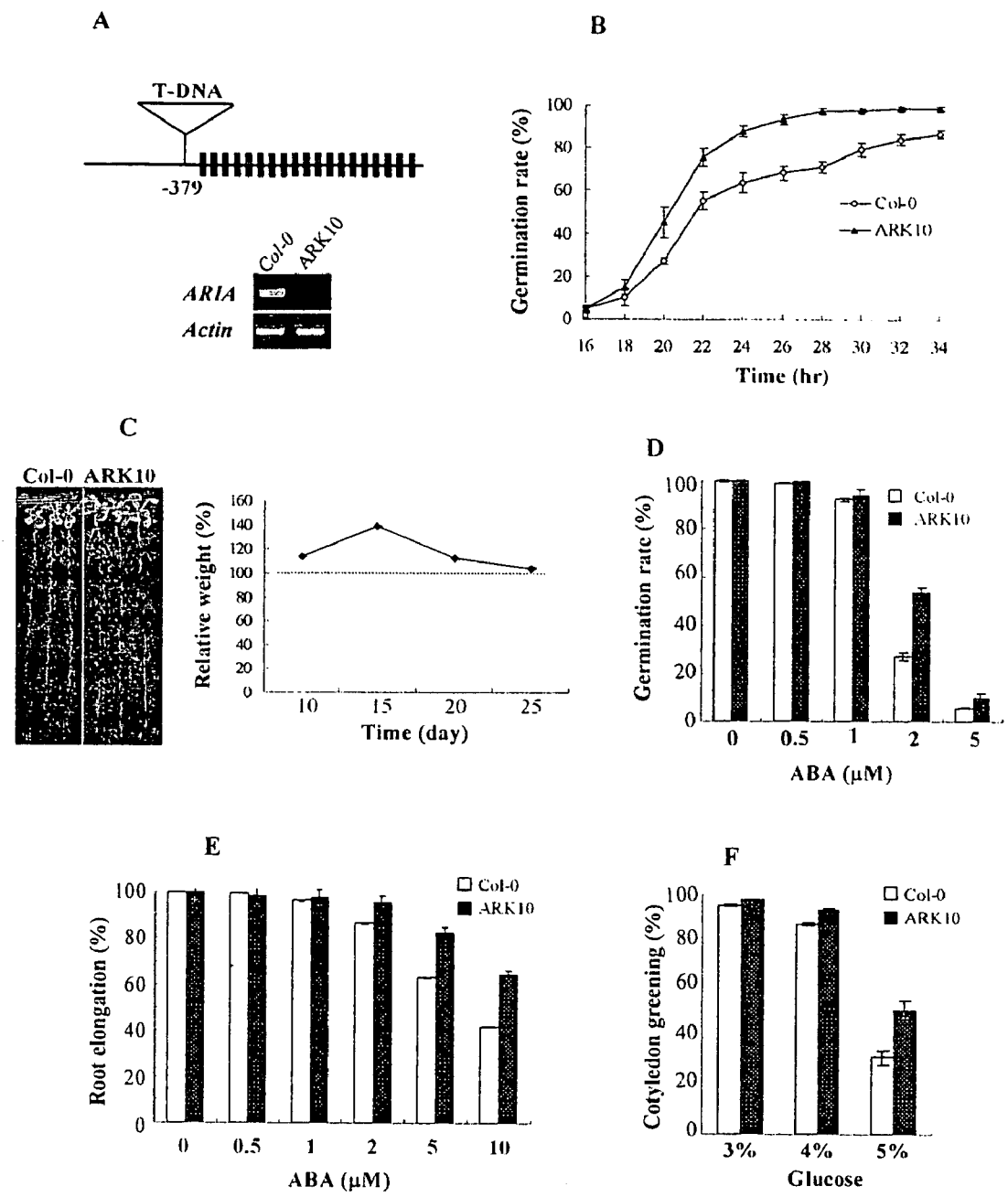

FIG. 4 Phenotypes of an aria knockout mutant. A, Schematic diagram of T-DNA insertion mutant. Top, the position of T-DNA insertion is presented. Bottom, expression levels of ARIA in wild type (Col-0) and the aria mutant (ARK10) plants determined by RT-PCR. B, Germination assy. Germination rates were determined as in FIG. 3A on MS medium, (triplicates, n=36 each). C, Growth of the aria mutant seedlings. Left panel, seedlings grown on MS medium for two weeks. Right panel, relative weight of aerial parts of soil-grown plants compared with that of Col-0 plants. The data point represents the mean of six determinations (n=6 each). D, ABA dose-response of germination. Germination assays were carried out on sucrose-free MS media containing various concentrations of ABA (triplicates, n=50 each). E, ABA dose-response of primary root elongation. Seeds were germinated on ABA-free MS medium for three days, transferred to media containing various concentrations of ABA, and the primary root elongation after the transfer was measured 5 days after the transfer (triplicates, n=6 each). The control growth rates of Col-0 and ARK10 on ABA-free medium are 24.1 and 32.6 mm, respectively. F, Glucose response. Seeds were germinated and grown on MS media containing 3%, 4%, or 5% glucose for 6 days before counting plants with green cotyledons (triplicates, n=30 each).

Figure 5:
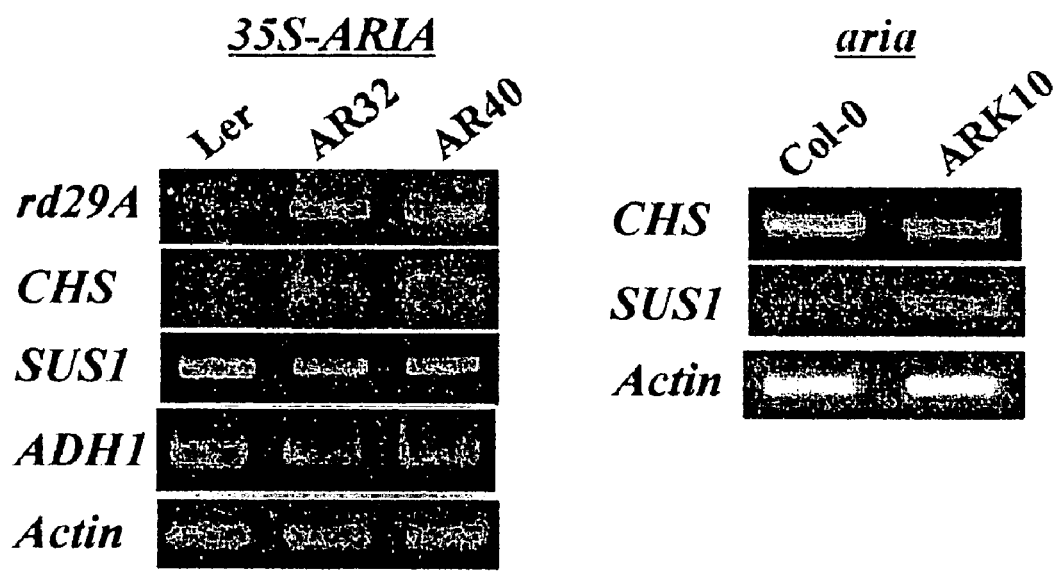

FIG. 5 Expression of ABA-responsive genes in 35S-ARIA and aria plants. RNA levels were determined by RT-PCR using total RNA isolated from two-week-old seedlings. The number of amplification cycles is different for different genes and for overexpression and knockout lines.

DETAILED DESCRIPTION OF THE INVENTION

Isolation of ABF2 Interacting Proteins by Yeast Two-hybrid Screens

We carried out yeast two-hybrid screens to isolate ABF2-interacting proteins (Chien et al., 1991; Gyuris et al., 1993). Since ABF2 has transcriptional activity (Choi et al., 2000), bait constructs were prepared employing partial fragments of ABF2 (FIG. 1A), to reduce the background activity. A cDNA expression library representing RNA from ABA-treated *Arabidopsis* seedlings (Choi et al., 2000) was then used to transform a yeast strain containing each bait construct. We recovered five positive clones that interacted with the variable region (amino acids 234–337) of ABF2. Insert analysis of the clones showed that two of them (Group 1) encoded a transcription factor, which will be reported elsewhere. Remaining three clones (Group 2) encoded an arm repeat protein (see below). The Group 2 clones did not interact with nuclear lamin or with the corresponding regions of ABF3 and ABF4 (FIG. 1B), indicating that they specifically interacts with ABF2.

Figure 1:
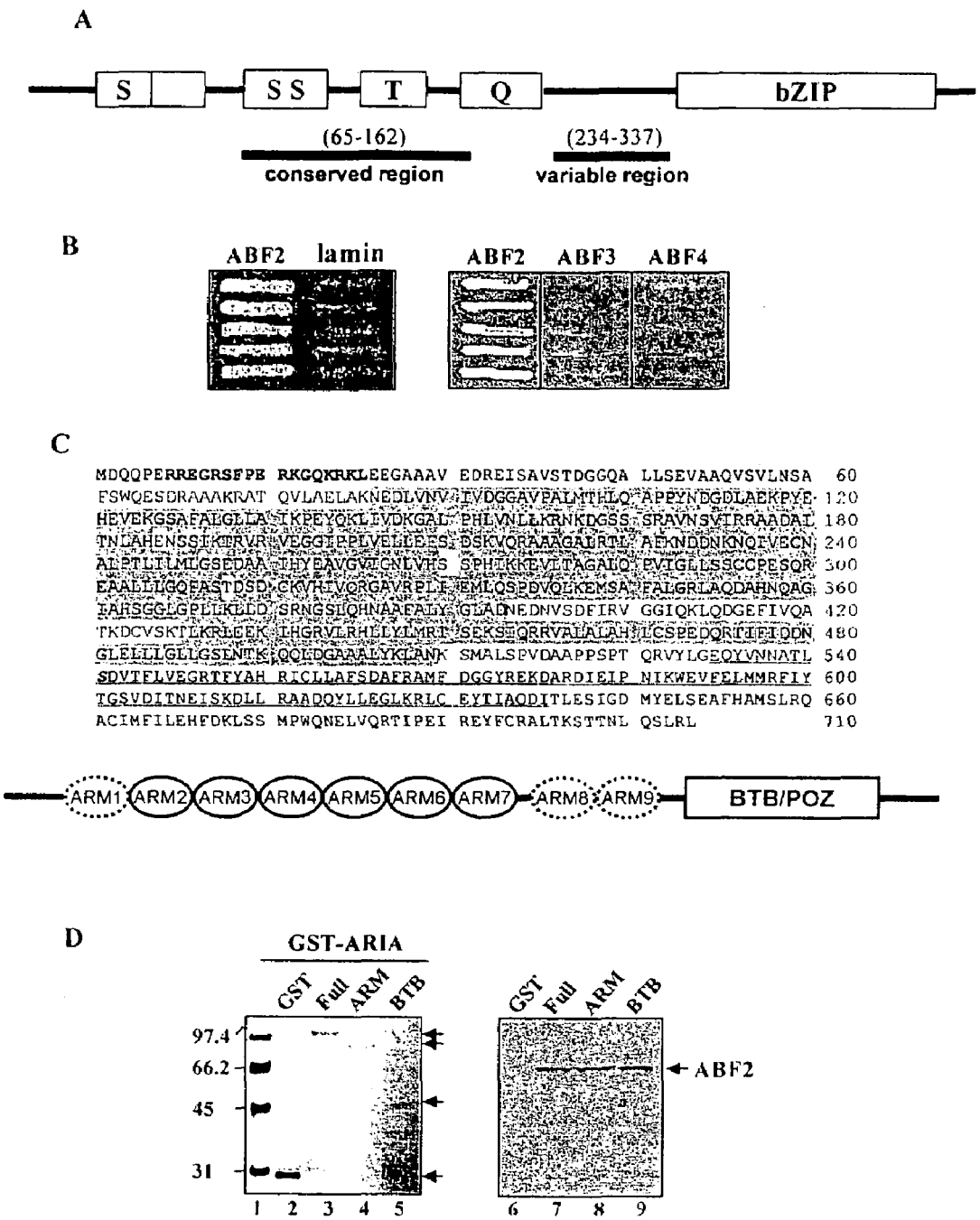

The longest open reading frame (ORF) of the Group 2 clones encoded a protein containing 705 amino acid residues. The ORF was missing the initiation codon. Database search and subsequent isolation/sequencing of the full-length cDNA (SEQ ID NO: 1) revealed that the protein consists of 710 amino acid residues with a predicted molecular weight of 78 kD (SEQ ID NO: 2) (FIG. 1C). The ABF2-interacting protein, designated as ARIA (Arm repeat protein Interacting with ABF2), has 9 copies of arm repeat in the N-terminal half, with arm 1, 8, and 9 being less-well conserved. Additionally, it has a BTB/POZ domain in the C-terminal region. The gene encoding ARIA (At5g19330) is composed of 19 exons and ARIA exhibits the highest sequence identity (59%) to another *Arabidopsis* arm repeat protein (At5g13060) of unknown function.

ARIA Interacts with ABF2 in vitro

The interaction between ARIA and ABF2 was confirmed by in vitro binding assay. Recombinant proteins (FIG. 1D, lanes 3–5) containing the entire ARIA coding region, the arm repeat region, or the BTB domain as a fusion to the glutathione-S-transferase (GST) were prepared. Their interaction with the full-length ABF2 was then determined by GST pulldown assay, using in vitro translated ABF2 labeled with $^{35}$S. As shown in FIG. 1D, ABF2 was retained by the GST-full-length ARIA fusion protein (lane 7), whereas it was not retained by GST alone (lane 6). Thus, full-length ARIA interacted with ABF2. Similarly, the fragments containing the arm repeat region or the BTB domain also interacted with ABF2 (lanes 8 and 9). The stronger band intensity observed with the BTB domain (lane 9) suggested that ABF2 bound the domain more strongly.

Expression Patterns and Subcellular Localization of ARIA Are Similar to Those of ABF2

The ABA- and stress-inducibility of ARIA expression was examined by RNA gel blot analysis. Like ABF2, whose expression is induced by ABA and high salt (Choi et al., 2000), ARIA transcript level was enhanced by ABA and high salt treatments (FIG. 2A). To investigate the temporal and spatial expression patterns of ARIA in detail, histochemical β-glucuronidase (GUS) staining of transgenic plants carrying an ARIA promoter-GUS fusion construct was conducted. Strong GUS activity was detected in the radicles of germinating seedlings (data not shown) and in the roots of young seedlings (FIG. 2B, a). In older seedlings (FIG. 2B, b), leaves exhibited stronger GUS activity than roots. In particular, the vascular tissues and the guard cells were stained strongly (FIG. 2B, c). In roots of older seedlings, GUS activity was detected mainly in lateral roots rather than in the primary roots (FIG. 2B, d). The vascular region was more strongly stained than the epidermal tissues (FIG. 2B, e, upper panel), and very strong GUS activity was observed in lateral root primordia and in the basal part of the lateral roots (FIG. 2B, e, lower panel). Anthers, filaments, stigma, and the abscission zone of immature siliques exhibited strong GUS activity among the reproductive organs (FIG. 2B, f–h). Embryos were also stained strongly (FIG. 2B, a, inset). In summary, ARIA promoter activity was detected in embryos and most of the vegetative and reproductive organs. The temporal and spatial expression patterns of ARIA are very similar to those of ABF2. For instance, ABF2 promoter is very active in most of the vegetative tissues, especially, in lateral roots, leaf veins, and guard cells. Besides, ABF2 is also strongly expressed in anthers, filaments and stigma among the floral organs.

ABF2 is a transcription factor and, as shown in FIG. 2C (top panel), is localized in the nucleus. We noticed that ARIA has a nuclear localization signal near its N-terminus (FIG. 1C), suggesting that it may be localized in the nucleus. To determine the intracellular localization of ARIA, transgenic plants harboring an ARIA-GFP (green fluorescent protein) fusion construct were generated, and the localization of the fusion protein was determined. FIG. 2C (middle panel) shows that GFP was localized in the nucleus, indicating that ARIA is nuclear-localized. GFP was also detected in the periphery of cells. It appears that ARIA is localized in the cell membrane as well.

Overexpression of ARIA Affects ABA and Osmolarity Sensitivities During Germination To investigate the in vivo function of ARIA, we generated and analyzed ARIA overexpression lines. Transgenic *Arabidopsis* plants expressing ARIA under the control of 35S promoter were generated (see Methods), and, after preliminary analysis of seven T3 homozygous lines, ABA/stress-related phenotypes of two representative lines were investigated in more detail.

ARIA overexpression lines did not exhibit significant growth phenotypes under normal condition except slightly (~1 hr) delayed germination (data not shown). However, ARIA overexpression affected ABA sensitivity during germination. ABA dose-response analysis (FIG. 3A) showed that germination of 35S-ARIA transgenic seeds was more severely inhibited by ABA than wild type seeds, especially at medium concentrations (1 and 2 µM) of ABA. Thus, ARIA overexpression enhanced ABA sensitivity during seed germination. In addition, germination of the transgenic seeds was more sensitive to mannitol, glucose, and NaCl (FIG. 3B), indicating that ARIA overexpression resulted in hypersensitive response to high osmolarity.

We also investigated the responses of 35S-ARIA seedlings to various abiotic stresses and found that they are less sensitive to high salt. For example, the survival rate of wild type plants at 100 mM NaCl was 55%, whereas those of 35S-ARIA plants were 81% (AR40) and 72% (AR32), respectively (FIG. 3C). At 125 mM NaCl, 38% (AR40) or 36% (AR32) of the transgenic plants survived, whereas the wild type survival rate was 11%. Thus, ARIA overexpression lines were more tolerant to high salinity condition.

Phenotypes of an Aria Mutant

To gain further insights into the in vivo function of ARIA, we analyzed the aria mutant phenotypes. A mutant, in which a T-DNA is inserted in the promoter region of ARIA (FIG. 4A), was obtained from the *Arabidopsis* stock center and, after the confirmation of T-DNA insertion (see Methods) and the abolishment of ARIA expression (FIG. 4A), various phenotypes were scored.

Germination assay (FIG. 4B) showed that the mutant seeds germinated more efficiently than wild type seeds under normal growth condition, although the degree of difference was not high. Postgermination growth of the aria mutant was also more efficient; i.e., aria seedlings were larger than wild type plants, as shown in FIG. 4C. They developed normally, however, and the fully-grown mutant seedlings were of similar size to the wild type plants, indicating that the mutation affected the growth of young seedlings only. Together, the observations demonstrate that ARIA is a negative regulator of seed germination and young seedling growth.

The aria mutant also exhibited altered ABA response. ABA dose-response analysis of germination (FIG. 4D) revealed that the mutant seed germination was les sensitive to ABA inhibition than wild type seeds at high concentrations of ABA (i.e., 2 and 5 µM), indicating that their germination was partially insensitive to ABA. Similarly, primary root elongation of aria plants was less sensitive to ABA-inhibition than wild type plants at higher ABA concentrations (i.e., 2, 5 and 10 µM) (FIG. 4E).

Glucose inhibits the shoot development (i.e., cotyledon greening, cotyledon expansion, and true leaf formation) at high concentrations, and the inhibition process is dependent on ABA (Jang et al., 1997; Leon and Sheen, 2003). To see whether ARIA is involved in the process, we determined the glucose sensitivity of aria plants. FIG. 4F shows that cotyledon greening of wild type plants was gradually inhibited as glucose concentration in the medium increased. The aria mutant plants were also responsive to glucose in a similar manner, but the degree of inhibition was lower than that of the wild type plants. The differential response was not observed with mannitol, i.e., it was not osmotic response (data not shown). The result demonstrates that ARIA is a necessary component for the glucose-inhibition of shoot development.

ARIA Affects the Expression of ABA-Responsive Genes

To examine whether ARIA affects ABF2-regulated gene expression, we determined the expression levels of a number of ABF2-responsive genes in 35S-ARIA plants. Coupled reverse transcription and polymerase chain reactions (RT-PCR) (FIG. 5) showed that the RNA levels of rd29A (Yamaguchi-Shinozaki and Shinozaki, 1994) and CHS (Feinbaum and Ausubel, 1988), which are down-regulated by ABF2 under normal condition but up-regulated under high salt condition, were higher in 35S-ARIA plants. On the other hand, SUS1 (Martin et al., 1993) and ADH1 (de Bruxelles et al., 1996) expression levels, which are down-regulated by ABF2 under normal condition, were slightly lower than wild type levels. In aria mutant plants, CHS RNA level was reduced, whereas SUS1 RNA level was elevated, further suggesting the regulatory role of ARIA in their expression. Thus, over- or under-expression of ARIA altered the expression of several ABF2-regulated genes, suggesting that it may be involved in the ABF2-dependent gene regulation process.

Discussion

We described an arm repeat protein designated as ARIA, which specifically interacts with ABF2. In animals, arm proteins are involved in a variety of cellular functions such as cell-contact, signal transduction, tumor suppression, and nuclear import (Hatzfeld, 1999; Andrade et al., 2001). In plants, their functions are largely unknown except for a few genes. ARC1 and PHOR1 are regulators of self-incompatibility and GA signaling, respectively, as mentioned earlier (Stone et al., 1999; Amador et al., 2001). A tobacco arm repeat protein, NtPUB4, which interacts with a receptor-like kinase, has been suggested to be a developmental regulator (Kim et al., 2003). The majority (approximately 40%) of Arabidopsis arm repeat proteins, including ARC 1 and PHOR1, contain the U-box motif found in a subclass of E3 unbiquitin ligases (Coates, 2003; Mudgil et al., 2004). Many of them therefore may participate in the ubiquitin-dependent protein degradation process. ARIA, however, does not contain the U-box motif. Instead, it possesses another conserved sequence motif, BTB/POZ domain. Sequence comparison indicates that only two Arabidopsis proteins, including ARIA, have both arm repeat and BTB/POZ domain. The BTB/POZ domain is found in many transcription factors and in some actin-binding proteins in animals (Aravind and Koonin, 1998; Collins et al., 2001). Most recent studies show that some BTB domain proteins are substrate-specific adapters for the CUL-3-based E3 ubiquitin ligases (van den Heuvel, 2004). Although arm repeat and BTB domain proteins play diverse roles, the basic functions of the two motifs are to mediate protein—protein interactions. Thus, ARIA has the potential to form complexes with other proteins or to function as a scaffold.

The physiological relevance of the ABF2-ARIA interaction was supported by their similar expression patterns. Expression of both ABF2 and ARIA is induced by ABA and high salt (FIG. 2) (Choi et al., 2000). Both are highly expressed in vegetative tissues (especially, in lateral roots, leaf vascular tissues, and guard cells) and in reproductive organs (i.e., anthers, filaments, stigma, and abscission zone). Furthermore, both proteins are localized in the nucleus (FIG. 2), although ARIA is also found in the cell membrane or cell wall region.

Our data on the in vivo function of ARIA further support the physiological significance of the ABF2-ARIA interaction. ARIA overexpression enhanced ABA and osmolarity sensitivities at the germination stage. During subsequent seedling growth, it enhanced salt tolerance. Disruption of its expression, on the other hand, promoted germination/seedling growth and impaired glucose response. Several of the 35S-ARIA and aria mutant phenotypes are similar to those of 35S-ABF2 and abf2 plants. For instance, delayed germination of overexpression lines, faster germination/growth of mutant seedlings, salt tolerance of overexpression lines, and glucose insensitivity of knockout mutants were also observed with ABF2 (Kim et al., 2004). Furthermore, we observe altered expression of several ABF2-responsive genes in 35S-ARIA and aria plants (FIG. 5), suggesting that ARIA affects ABF2-regulated gene expression.

Our results indicate that ARIA is a positive component of ABA signaling. ABA sensitivity was enhanced by its overexpression and impaired by its knockout mutation. Germination was delayed by its overexpression and promoted by its mutation. Also, other ABA-associated processes such as osmolarity sensitivity and sugar response were positively and negatively affected by ARIA overexpression and its mutation, respectively. Two observations are worthy to be mentioned regarding the role of ARIA in ABA response. First, most of the ARIA overexpression and knockout phenotypes are relatively weak or partial (FIGS. 3 and 4), although they are consistently observed. This implies that the function of ARIA might be redundant. As mentioned before, there is an arm repeat/BTB domain protein in the Arabidopsis genome, which is highly homologous to ARIA not only in the amino acid sequence but also in its gene structure (data not shown), and, thus, functional redundancy between the two proteins can be speculated. Another observation is that ARIA affects only a subset of ABA-dependent processes. ABA sensitivity during germination and young seedling growth was affected by ARIA. However, other ABA-dependent processes, such as stomatal closure and abiotic stress responses other than salt tolerance, were not significantly affected by it (data not shown).

The altered expression of several ABF2-regulated genes (FIG. 5) suggests that ARIA affects the ABF2-dependent gene expression. We do not know the biochemical mechanism of ARIA function at present. However, it can be speculated that it may function as a coactivator or repressor of ABF2. In animals, the arm protein, β-catenin, has been demonstrated to be a transcriptional coactivator; i.e., it translocates into the nucleus in response to a hormone signal and form complexes with transcription factors to activate target gene expression (Polakis, 2000). The BTB/POZ domain, on the other hands, is known to mediate transcriptional repression by recruiting transcriptional corepressors, which, in turn, recruit histone deacetylase to suppress transcription (Collins et al., 2001). The BTB/POZ domain is also involved in protein degradation (van den Heuvel, 2004). Thus, ARIA might be involved in the stability control of ABF2 or other proteins that possibly might associate with it. Since ARIA possesses two protein—protein interaction domains, another possibility is that it may function as an adaptor for ABF2 to form a protein complex.

Whatever the biochemical mechanism(s) of ARIA function may be, our data indicate that overexpression of ARIA enhances the salt tolerance of *Arabidopsis* plants. The result suggests that expression of ARIA can be engineered to promote the salt tolerance of plants, and thus it will be possible to develop salt-tolerant plants utilizing the ARIA gene.

EXAMPLES

Example 1

DNA Manipulation and RNA Gel Blot Analysis

DNA manipulation and RNA gel blot analyses were performed according to the standard methods (Sambrook and Russel, 2001). DNA sequencing was done on ABI 310 GENETIC ANALYZER (Applied Biosystems). RNA was isolated by the method of Chomczynski and Mackey (1995) and purified further by LiCl precipitation and ethanol precipitation. ABA, salt, cold, and drought treatments of *Arabidopsis* seedlings were conducted as described (Choi et al., 2000). For RNA gel blot analysis, 25 µg of total RNA was separated on 1.1% formaldehyde agarose gel, transferred to nylon membrane (HYBOND-XL, Amersham Pharmacia Biotech), and fixed using STRATAGENE'S UV CROSSLINKER (MODEL 2400). Hybridization was carried out at 65° C. for 18–24 hr in RAPID-HYB BUFFER (Amersham Pharmacia Biotech), using a $^{32}$P-labelled DNA fragment containing the less-well conserved region (amino acid position 336–554) of ARIA as a probe. Filters were washed sequentially as follows: twice in 2×SSC (1×SSC is 0.15 M NaCl, 0.015 M sodium citrate) for 10 min at room temperature, twice in 0.2×SSC for 10 min at room temperature, twice in 0.2×SSC for 10 min at 65° C. Exposure was done at −70° C. RT-PCR was carried out by processing 0.5 µg of total RNA according to the manufacturer's instruction, employing the ACCESS RT-PCR SYSTEM (Promega). Primer sets, including the actin primers used for control reaction (*Arabidopsis* actin-1 gene, Accession number M20016), were described previously (Kang et al., 2002). RNA samples were confirmed to be free of contaminating DNA by using the actin primer set that spans an intron and, when possible, also by using primer sets spanning an intron(s). The number of PCR cycles was variable depending on specific genes (generally 20–30 cycles), within the linear range of PCR amplification. The results of RT-PCR were confirmed by several independent reactions.

Example 2

Yeast Techniques and Two-hybrid Screening

Yeast growth and transformation were according to the standard techniques (Guthrie and Fink, 1991). Two-hybrid screens were carried out employing the MATCHMAKER LEXA TWO-HYBRID SYSTEM (Clontech), with some modifications. Bait constructs were prepared by cloning two partial fragments of ABF2 into pGILDA (Clontech), which carries the LexA DNA binding domain under the control of the GAL1 promoter and the HIS3 marker gene. The ABF2 fragments, spanning amino acid residues 65–162 (conserved region) and 234–337 (variable region), respectively, were prepared by PCR (primer sets, 5'-GCTAGTGGTGTGGT-TCCAGTT C-3' (SEQ ID NO: 3) and 5'-gagagctcgagCT-GAGCTCTTGCAGCAACCTG-3' (SEQ ID NO: 4), and 5'-CCAATCATGCCTAAGCAGCC-3' (SEQ ID NO: 5) and 5'-gagagctcgagCTCTACAAC TTTCTCCACAGTG-3' (SEQ ID NO: 6), respectively), and, after digestion with Xho I, ligated with pGilda, which in turn was prepared by Bam HI digestion, Klenow fill-in reaction, and Xho I digestion. The bait constructs were then individually introduced into the reporter yeast, EGY48 (MATα, his3, trp1, URA3::LexA$_{op(x8)}$-LacZ, LexA$_{op(x6)}$-LEU2), by transformation. The EGY48 strain carries two reporter genes, LEU2 and LacZ, integrated into the chromosome. Large-scale transformation for the screening was carried out as described (Choi et al., 2000). The reporter yeast was transformed with library plasmid DNA representing cDNA of ABA/salt-treated *Arabidopsis* seedlings (Choi et al., 2000). Transformed yeast was grown on Gal/Raf/CM-His-Leu-Trp-Ura medium for 5–7 days, and positive colonies were identified by colony lift β-galactosidase assay. The Leu$^+$/LacZ$^+$ positive colonies were purified by streaking on the same selection medium followed by another round of β-galactosidase assay. For each reporter yeast, 6.6 million transformants were screened, and five positive clones were obtained from the variable region bait, whereas no positive clones were obtained from the conserved region bait. Specificity of the interaction of the positive clones was tested by re-transforming the reporter yeast with the plasmid DNA rescued from the clones (see below).

Plasmid rescue and insert DNA analysis were carried out as described (Choi et al., 2000). Sequencing of the plasmid DNA rescued from the positive clones revealed that three of them (clones 12, 20, and 24) encoded an arm repeat protein (At5g19330) and two of them (clones 17 and 27) encoded a transcription factor. The longest arm protein clone was missing the first five amino acid residues. Full-length gene was isolated by PCR using the primer set, 5'-GGATCGTCTTTTACTTTGTGAACG-3' (SEQ ID NO: 7) and 5'-CATTCAA GAC CGA TTG TGATCAG-3' (SEQ ID NO: 8), and 1 µg of library DNA. The PCR product, which contains the entire coding region and 5' (208 bases) and 3' (24 bases) additional sequences, was cloned into the ZERO BLUNT® TOPO PCR CLONING KIT (Invitrogen) and sequenced fully. The correctness of its nucleotide sequence was confirmed by comparing it with the genomic sequence on the *Arabidopsis* database.

Example 3

In vitro Binding Assay

GST-ARIA fusion constructs were prepared by cloning PCR fragments of various portions (full-length, amino acids 1–518, and amino acids 511–710) of ARIA into the Sma I site of pGEX-6P-2 (Amersham Pharmacia Biotech). Constructs were used to transform BL21 cells, and transformed cells were grown in 2×YT medium containing 50 µg/ml ampicillin overnight. The cultures were diluted 100-fold and grown to A$_{600}$ of 0.6 at 30° C. (BTB construct) or 37° C. (Full-length and ARM constructs). The expression of recombinant proteins was induced with 0.5 mM isopropyl-β-D-thiogalactopyranoside for 3 hr. At the end of the induction, cells were pelleted down by centrifugation, resuspended in 6 ml of PBS (0.14 M NaCl, 2.7 mM KCl, 10.1 mM Na$_2$HPO$_4$, 1.8 mM KH$_2$PO$_4$, PH7.3), and sonicated. The lysate was cleared of cell debris by centrifugation and further purified according to the supplier's instruction. For in vitro translation of ABF2, full-length ABF2 cloned into pCITE (Novagen), was processed with the TNT® IN VITRO TRANSLATION KIT (Promega) in the presence of $^{35}$S-Met according to the manufacturer's instruction.

For binding assay, GST-ARIA fusion proteins (0.5 µg) were incubated with the Glutathione-Sepharose 4B resins for 1 hr at 4° C. in a binding buffer (50 mM Tris, pH 8.0, 100 mM NaCl, 10% glycerol, 0.5% Triton X-100, 1 mM PMSF). In vitro-translated, $^{35}$S-labeled ABF2 was then added and incubation was continued for 2 hr with constant rotation. The resins were washed five times with the binding buffer and resuspended in SDS-polyacrylamide gel electrophoresis sample buffer. The proteins were separated on 15% SDS-polyacrylamide gel and visualized by autoradiography.

Example 4

Histochemical GUS Staining

A 2.1 kb promoter fragment was prepared by PCR, using the primer set, 5'-GATCCGAAG AAGAGGAGAGATC-3' (SEQ ID NO: 9) and 5-GCCACGCTGTCTTCTTTCACTA-CACT AAA AAATACAGC-3' (SEQ ID NO: 10), and cloned into the Hind III-Xba I sites of pBI101.2. The construct was introduced into *Arabidopsis* (Ler) by transformation, and T2 or T3 generation plants were used for the analysis of GUS activity. GUS staining was performed according to Jefferson et al. (1987). Whole plants or tissues were immersed in 1 mM 5-bromo-4-chloro-3-indolyl-β-glucuronic acid (X-gluc) solution in 100 mM sodium phosphate, pH 7.0, 0.1 mM EDTA, 0.5 mM ferricyanide, 0.5 mM ferrocyanide, and 0.1% Triton X-100 for 24 hr at 37° C. Chlorophyll was cleared from the tissues by ethanol series: 35%, 50%, and 70%.

Example 5

Subcellular Localization

To prepare the 35S-ARIA-GFP fusion construct, the entire coding region of ARIA was prepared by PCR, and after digestion with Nco I-Spe I, cloned into the same sites of pCAMBIA1302 (CAMBIA). The construct was introduced into *Arabidopsis* (Col-0) by transformation, and T1 plants were used for GFP localization analysis. Nuclei were visualized by propidium iodide (PI)-staining. Roots of 10-day-old transgenic seedlings were used for the green (GFP localization) and red (PI) fluorescence analysis using a confocal microscope (Leica, TCS-NT).

To investigate ABF2 localization, the coding region of ABF2 was inserted in front of the GUS coding region of pBI221 in frame. Onion epidermal cells were then transiently transformed with the ABF2-GUS construct by particle bombardment using PDS 1000 (Bio-Rad). GUS activity was determined by X-gluc (5-bromo-4-chloro-3-indolyl-β-glucuronic acid) staining after 24 hr at 23° C. Nuclei were visualized by 4',6-diamidino-2-phenylindole (DAPI) staining and observed under a fluorescence microscope (OLYMPUS BX51).

Example 6

Overexpresion and Knockout Mutant Lines

To prepare the 35S-ARIA construct, the coding region of ARIA was prepared by PCR, using primers 5'-cgcggatc-cATGGACCAACAACCGGAGAGG-3' (SEQ ID NO: 11) and 5'-gcgggatcc CAACCTCAAG CTTTG CAGGTT TG-3' (SEQ ID NO: 12), and, after digestion with Bam HI, cloned into the Bam HI site of pBI121 lacking the GUS coding region. Transformation of *Arabidopsis* (Ler) was according to the vacuum infiltration method (Bechtold and Pelletier, 1998), using *A. tumefaciens* strain GV3101. Seven homozygous lines were recovered and, after preliminary analysis, two representative lines (T4) were chosen for detailed analysis.

To establish aria mutant lines, four putative ARIA knock-out mutant lines were obtained from the *Arabidopsis* Stock Center. The stock seeds were sown and grown on soil, and seeds were harvested from individual plants. To choose T-DNA insertion lines with single integration, segregation ratio of kanamycin resistance (Kan$^R$) was tested, and homozygous sublines were established from those segregating at 3:1 ratio of Kan$^R$: Kan$^S$. Genomic DNA was isolated from the sublines and the integration of T-DNA at the annotated site was confirmed by the sequencing of PCR fragments. We were able to identify one insertion line (SALK_143439) with a single T-DNA insertion at the annotated site among the four putative lines. T-DNA is inserted at −379 from the translation start site. Expression analysis by RT-PCR showed that ARIA expression is abolished in the insertion line. For phenotype analysis, two sublines (ARK5 and ARK10) were used. Same results were obtained from them and those from AR10 are presented.

Example 7

Phenotype Analysis

*Arabidopsis thaliana* ecotypes Landsberg erecta (Ler) and Columbia (Col-0) were used. Plants were grown under long day condition (16 hr light/8 hr dark cycle) at 22° C., on 1:1:1 mixture of vermiculite, perlite and peat moss or on MS plates. Soil-grown plants were irrigated with 0.1% Hyponex once every week. For general aseptic growth, seeds were sterilized with 70% ethanol for 5 min and then with 30% household bleach for 5 min, washed 5 times with sterile water, and plated on MS medium (Murashige and Skoog, 1962) supplemented with 1% sucrose and solidified with 0.8% Phytoagar.

For germination test, seeds collected at the same time were plated, unless stated otherwise, on MS medium supplemented with 1% sucrose and other supplements (i.e., ABA, mannitol, glucose, and NaCl), and radicle emergence was examined at various time points. For ABA dose-response analysis of germination, sucrose was omitted from the media. Phenotype analyses other than germination assay were performed on MS medium supplemented with 1% sucrose and also with ABA, glucose, or mannitol as specified in the Figure legend. For root elongation assay, plants were grown at vertical position.

REFERENCES

Amador V, Monte E, Garcia-Martinez J L, and Prat S (2001) Gibberellins signal nuclear import of PHOR1, a photoperiod-responsive protein with homology to *Drosophila* armadillo. Cell 106: 343–354

Andrade M A, Petosa C, O'Donoghue S I, Muller C W, Bork P (2001) Comparison of ARM and HEAT protein repeats. J Mol Biol 309: 1–18

Aravind L, Koonin E V (1998) Fold prediction and evolutionary analysis of the POZ domain: structural and evolutionary relationship with the potassium channel tetramerization domain. J Mol Biol 285: 1353–1361

Bardwell V J, Treisman R (1994) The POZ domain: a conserved protein—protein interaction motif. Genes Dev 8: 1664–1677

Bechtold N, Pelletier G (1998) In planta *Agrobacterium*-mediated transformation of adult *Arabidopsis thaliana* plants by vacuum infiltration. Methods Mol Biol 82: 259–266 de Bruxelles G L, Peacock W J, Dennis E S, Dolferus R (1996) Abscisic acid induces the alcohol dehydrogenase gene in *Arabidopsis*. Plant Physiol 111: 381–391

Cao H, Glazebrook J, Clarke J D, Volko S, and Dong X (1997) The *Arabidopsis* NPR1 gene that controls systemic acquired resistance encodes a novel protein containing ankyrin repeats. Cell 88: 57–63

Chien C T, Bartel P L, Sternglanz R, Fields S (1991) The two-hybrid system: a method to identify and clone genes for proteins that interact with a protein of interest. Proc Natl Acad Sci USA 88: 9578–9582

Choi H, Hong J, Kang J, Kim S Y (2000) ABFs, a family of ABA-responsive element binding factors. J Biol Chem 21: 1723–1730

Chomczynski P, Mackey K (1995). Modification of the TR1 reagent procedure for isolation of RNA from polysaccharide- and proteoglycan-rich sources. BioTechniques 19: 942–945

Coates J C (2003) Armadillo repeat proteins: beyond the animal kingdom. Trends Cell Biol 13: 463–71

Collins T, Stone J R, Williams A J (2001) All in the family: the BTB/POZ, KRAB, and SCAN domains. Mol. Cell. Biol 21: 3609–3615

Feinbaum R L, Ausubel F M (1988) Transcriptional regulation of the *Arabidopsis thaliana* chalcone synthase gene. Mol Cell Biol 8: 1985–1992

Finkelstein R R, Gampala S S, Rock C D (2002) Abscisic acid signaling in seeds and seedlings. Plant Cell 14 Suppl: S15–45.

Gu T, Mazzurco M, Sulaman W, Matias D D, Goring D R (1998) Binding of an arm repeat protein to the kinase domain of the S-locus receptor kinase. Proc Natl Acad Sci USA 95: 382

Guthrie C, Fink G R eds (1991) Guide to Yeast Genetics and Molecular Biology, Methods Enzymol 194

Gyuris J, Golemis E, Chertkov H, Brent R (1993) Cdi1, a human GI and S phase protein phosphatase that associates with Cdk2. Cell 75: 791–803

Hatzfeld M (1999) The armadillo family of structural proteins. Int Rev Cytol 186: 179–224 van den Heuvel S (2004) Protein degradation: CUL-3 and BTB—partners in proteolysis. Curr Biol 14: R59–61

Jang J-C, Leon P, Zhou L, Sheen J (1997) Hexokinase as a sugar sensor in higher plants. Plant Cell 9: 5–19

Jefferson R A, Kavanagh T A, Bevan M W (1987) GUS fusions: β-glucuronidase as a sensitive and versatile gene fusion marker in higher plants. EMBO J. 20: 3901–3907

Kang J, Choi H, Im M, Kim S Y (2002) *Arabidopsis* basic leucine zipper proteins that mediate stress-responsive abscisic acid signaling. Plant Cell 14: 343–357

Kim M, Cho H S, Kim M, Lee J H, Pai H S (2003) CHRK1, a chitinase-related receptor-like kinase, interacts with NtPUB4, an armadillo repeat protein, in tobacco. Biochim Biophys Acta 1651: 50–59

Kim S, Kang J, Cho D-I, Park J H, Kim S Y (2004) ABF2, an ABRE-Binding bZIP factor, is an essential component of glucose signaling and its overexpression affects multiple stress tolerance. Plant J, in press.

Leon P, Sheen J (2003) Sugar and hormone connections. Trends Plant Sci 8: 110–116

Martin T, Frommer W B, Salanoubat M, Willmitzer L (1993) Expression of an *Arabidopsis* sucrose synthase gene indicates a role in metabolization of sucrose both during phloem loading and in sink organs. Plant J 4: 367–377

Motchoulski A, Liscum E (1999) *Arabidopis* N PH3: A NPH1 photoreceptor-interacting protein essential for phototropism. Science 286: 961–964

Mudgil Y, Shiu S H, Stone S L, Salt J N, Goring D R (2004) A large complement of the predicted *Arabidopsis* ARM repeat proteins are members of the U-box E3 ubiquitin ligase family. Plant Physiol 134: 59–66.

Murashige T, Skoog F (1962). A revised medium for rapid growth and bioassay with tobacco tissue culture. Physiol Plant 15: 473–497

Peifer M, Berg S, Reynolds A B (1994) A repeating amino acid motif shared by proteins with diverse cellular roles. Cell 76: 789–791

Polakis P (2000) Wnt signaling and cancer. Genes Dev 14: 1837–1851

Ramanulu S, Bartels D (2002) Drought- and desiccation-induced modulation of gene expression in plants. Plant Cell Environ. 25: 141–151

Riggleman B, Wieschaus E, aSchedl P (1989) Molecular analysis of the armadillo locus: uniformly distributed transcripts and a protein with novel internal repeats are associated with a *Drosophila* segment polarity gene. Genes Dev 3: 96–113

Ryals J, Weymann K, Lawton K, Friedrich L, Ellis D, Steiner H Y, Johnson J, Delaney T P, Jesse T, Vos P, Uknes S (1997) The *Arabidopsis* NIM1 protein shows homology to the mammalian transcription factor inhibitor I kappa B. Plant Cell 9: 425–439

Sakai T, Wada T, Ishiguro S, Okada K (2000) RPT2: A signal transducer of the phototrophic response in *Arabidopsis*. Plant Cell 12: 225–236

Sambrook J, Russell D W (2001) Molecular Cloning: A laboratory Manual, $3^{rd}$ ed., Cold Spring Harbor Laboratory, Cold Spring Harbor, N.Y.

Shinozaki K, Yamaguchi-Shinozaki K, Seki M (2003) Regulatory network of gene expression in the drought and cold stress responses. Curr Opin Plant Biol 6: 410–417

Stone S L, Anderson E M, Mullen R T, Goring D R (2003) ARC1 is an E3 ubiquitin ligase and promotes the ubiquitination of proteins during the rejection of self-incompatible *Brassica* pollen. Plant Cell 15: 885–898

Stone S L, Arnoldo M, Goring D R A (1999) A breakdown of *Brassica* self-incompatibility in ARC1 antisense transgenic plants. Science 286: 1729–31

Uno Y, Furihata T, Abe H, Yoshida R, Shinozaki K, Yamaguchi-Shinozaki K (2000) *Arabidopsis* basic leucine zipper transcription factors involved in an abscisic acid-dependent signal transduction pathway under drought and high-salinity. Proc. Natl. Acad. Sci. USA 97: 11632–11637

Xiong L, Schumaker K S, Zhu J-K (2002) Cell signaling during cold, drought, and salt stress. Plant Cell 14: Suppl, S165–183

Yamaguchi-Shinozaki K, Shinozaki K (1994) A novel cis-acting element in an *Arabidopsis* gene is involved responsiveness to drought, low-temperature, or high-salinity stress. Plant Cell 6: 251–264

Zollman S, Godt D, Prive G G, Couderc J L, Laski F A (1994) The BTB domain, found primarily in zinc finger proteins, defines an evolutionarily conserved family that includes several developmentally regulated genes in *Drosophila*. Proc Natl Acad Sci USA 91, 10717–10721

The invention claimed is:

1. A method for producing a salt-tolerant plant comprising transforming a plant cell with a recombinant DNA molecule comprising a nucleotide sequence comprising SEQ ID NO:1 or encoding SEQ ID NO:2 operably linked to a promoter that functions in plant cells, regenerating a transformed plant from said plant cell, and further comprising the step of screening the transformants for increased tolerance to salt compared to non-transformed plants of the same species.

* * * * *